US010544267B2

(12) United States Patent
Knott et al.

(10) Patent No.: US 10,544,267 B2
(45) Date of Patent: Jan. 28, 2020

(54) METHOD FOR PRODUCING SILOXANES CONTAINING GLYCERIN SUBSTITUENTS

(71) Applicant: Evonik Degussa GmbH, Essen (DE)

(72) Inventors: Wilfried Knott, Essen (DE); Horst Dudzik, Essen (DE); Klaus-Dieter Klein, Mülheim an der Ruhr (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 16/315,833

(22) PCT Filed: Jul. 5, 2017

(86) PCT No.: PCT/EP2017/066756
§ 371 (c)(1),
(2) Date: Jan. 7, 2019

(87) PCT Pub. No.: WO2018/015152
PCT Pub. Date: Jan. 25, 2018

(65) Prior Publication Data
US 2019/0248959 A1    Aug. 15, 2019

(30) Foreign Application Priority Data
Jul. 22, 2016 (EP) .................................. 16180762

(51) Int. Cl.
| | | |
|---|---|---|
| *C08G 77/38* | (2006.01) | |
| *A61Q 19/00* | (2006.01) | |
| *A61K 8/892* | (2006.01) | |
| *C08L 83/04* | (2006.01) | |
| *C08K 5/06* | (2006.01) | |
| *A61K 8/891* | (2006.01) | |
| *C08K 5/01* | (2006.01) | |
| *C08K 5/1565* | (2006.01) | |
| *A61K 8/58* | (2006.01) | |
| *A61K 47/24* | (2006.01) | |
| *A61K 47/34* | (2017.01) | |
| *C07F 7/18* | (2006.01) | |
| *C08G 77/06* | (2006.01) | |
| *C08G 77/12* | (2006.01) | |
| *C08G 77/00* | (2006.01) | |

(52) U.S. Cl.
CPC .............. *C08G 77/38* (2013.01); *A61K 8/585* (2013.01); *A61K 8/891* (2013.01); *A61K 8/892* (2013.01); *A61K 47/24* (2013.01); *A61K 47/34* (2013.01); *A61Q 19/00* (2013.01); *C07F 7/1804* (2013.01); *C07F 7/1876* (2013.01); *C08G 77/06* (2013.01); *C08K 5/01* (2013.01); *C08K 5/06* (2013.01); *C08K 5/1565* (2013.01); *C08L 83/04* (2013.01); *A61K 2800/00* (2013.01); *A61K 2800/52* (2013.01); *C08G 77/12* (2013.01); *C08G 77/70* (2013.01)

(58) Field of Classification Search
None
See application file for complete search history.

(56) References Cited

U.S. PATENT DOCUMENTS

| | | |
|---|---|---|
| 3,775,452 A | 11/1973 | Karstedt |
| 4,908,228 A | 3/1990 | Lo |
| 5,371,161 A | 12/1994 | Knott |
| 5,475,127 A | 12/1995 | Klein et al. |
| 5,486,634 A | 1/1996 | Hahn et al. |
| 5,917,059 A | 6/1999 | Bruchmann et al. |
| 6,291,622 B1 | 9/2001 | Droese et al. |
| 6,307,082 B1 | 10/2001 | Klein et al. |
| 6,858,663 B2 | 2/2005 | Knott et al. |
| 7,018,458 B2 | 3/2006 | Knott et al. |
| 7,157,541 B2 | 1/2007 | Knott et al. |
| 7,196,153 B2 | 3/2007 | Burkhart et al. |
| 7,589,334 B2 | 10/2009 | Ferenz et al. |
| 7,612,159 B2 | 11/2009 | Burkhart et al. |
| 7,645,858 B2 | 1/2010 | Knott et al. |
| 7,754,778 B2 | 7/2010 | Knott et al. |
| 7,825,205 B2 | 11/2010 | Knott et al. |
| 7,825,206 B2 | 11/2010 | Neumann et al. |
| 7,825,209 B2 | 11/2010 | Knott et al. |
| 8,138,294 B2 | 3/2012 | Henning et al. |
| 8,247,525 B2 | 8/2012 | Schubert et al. |
| 8,283,422 B2 | 10/2012 | Schubert et al. |
| 8,309,664 B2 | 11/2012 | Knott et al. |
| 8,309,673 B2 | 11/2012 | Schubert et al. |

(Continued)

FOREIGN PATENT DOCUMENTS

| | | |
|---|---|---|
| DE | 19647395 A1 | 5/1998 |
| DE | 19648960 A1 | 5/1998 |

(Continued)

OTHER PUBLICATIONS

Written Opinion of the International Searching Authority; PCT/EP2017 /066756; dated Sep. 18, 2017 (Year: 2017).*
Amajjahe et al., U.S. Appl. No. 15/760,320, filed Mar. 15, 2018.
German language Written Opinion dated Sep. 18, 2017 in PCT/EP2017/066756 (5 pages).
International Search Report dated Sep. 18, 2017 in PCT/EP2017/066756 (2 pages).
Knott et al., U.S. Appl. No. 16/029,987, filed Jul. 9, 2018.
Knott et al., U.S. Appl. No. 16/140,573, filed Sep. 25, 2018.
Knott et al., U.S. Appl. No. 16/190,293, filed Nov. 14, 2018.
Schubert et al., U.S. Appl. No. 16/087,762, filed Sep. 24, 2018.

*Primary Examiner* — Clinton A Brooks
*Assistant Examiner* — Kofi Adzamli
(74) *Attorney, Agent, or Firm* — Philip P. McCann; Nexsen Pruet PLLC

(57) ABSTRACT

The invention relates to a method for producing siloxanes that have glycerin modifications and, at the same time, hydrophobic substituents. The invention further relates to a siloxane that has glycerin modifications and also hydrophobic side chains, wherein at least some of the glycerin modifications bear ketal groups, and to the use of said new siloxanes.

13 Claims, No Drawings

(56) References Cited

U.S. PATENT DOCUMENTS

| | | |
|---|---|---|
| 8,334,355 B2 | 12/2012 | Henning et al. |
| 8,455,603 B2 | 6/2013 | Ferenz et al. |
| 8,557,944 B2 | 10/2013 | Henning et al. |
| 8,598,295 B2 | 12/2013 | Henning et al. |
| 8,609,798 B2 | 12/2013 | Knott et al. |
| 8,623,984 B2 | 1/2014 | Henning et al. |
| 8,685,376 B2 | 4/2014 | Czech et al. |
| 8,722,834 B2 | 5/2014 | Knott et al. |
| 8,722,836 B2 | 5/2014 | Knott et al. |
| 8,729,207 B2 | 5/2014 | Hartung et al. |
| 8,772,423 B2 | 7/2014 | De Gans et al. |
| 8,779,079 B2 | 7/2014 | Henning et al. |
| 8,802,744 B2 | 8/2014 | Knott et al. |
| 8,841,400 B2 | 9/2014 | Henning et al. |
| 8,921,437 B2 | 12/2014 | Knott et al. |
| 8,946,369 B2 | 2/2015 | Henning et al. |
| 8,957,009 B2 | 2/2015 | Schubert et al. |
| 8,974,627 B2 | 3/2015 | Schubert et al. |
| 9,035,011 B2 | 5/2015 | Ferenz et al. |
| 9,334,354 B2 | 5/2016 | Ferenz et al. |
| 9,353,225 B2 | 5/2016 | Knott et al. |
| 9,481,695 B2 | 11/2016 | Knott et al. |
| 9,540,500 B2 | 1/2017 | Ferenz et al. |
| 9,695,202 B2 | 7/2017 | Henning et al. |
| 9,896,541 B2 | 2/2018 | Fiedel et al. |
| 9,975,909 B2 | 5/2018 | Schubert et al. |
| 10,087,278 B2 | 10/2018 | Lobert et al. |
| 10,099,211 B2 | 10/2018 | Knott et al. |
| 10,106,649 B2 | 10/2018 | Fiedel et al. |
| 2002/0161158 A1 | 10/2002 | Burkhart et al. |
| 2007/0128143 A1 | 6/2007 | Gruning et al. |
| 2008/0227923 A1 | 9/2008 | Klein et al. |
| 2010/0081781 A1 | 4/2010 | Schubert et al. |
| 2011/0230619 A1 | 9/2011 | Kuppert et al. |
| 2011/0301254 A1 | 12/2011 | Knott et al. |
| 2012/0068110 A1 | 3/2012 | Schubert et al. |
| 2012/0282210 A1 | 11/2012 | Henning et al. |
| 2013/0123530 A1 | 5/2013 | Boehm et al. |
| 2013/0345318 A1 | 12/2013 | Schubert et al. |
| 2015/0004112 A1 | 1/2015 | Ritter et al. |
| 2015/0004113 A1 | 1/2015 | Ritter et al. |
| 2016/0052849 A1* | 2/2016 | Souda .................. A61Q 19/00 525/479 |
| 2016/0130402 A1 | 5/2016 | Schubert et al. |
| 2017/0198099 A1 | 7/2017 | Knott |
| 2018/0016392 A1 | 1/2018 | Lobert et al. |
| 2018/0134850 A1 | 5/2018 | Knott et al. |
| 2018/0258228 A1 | 9/2018 | Amajjahe et al. |
| 2018/0319823 A1 | 11/2018 | Knott et al. |
| 2018/0355114 A1 | 12/2018 | Knott et al. |
| 2018/0355115 A1 | 12/2018 | Knott et al. |

FOREIGN PATENT DOCUMENTS

| | | |
|---|---|---|
| DE | 102008015756 A1 | 10/2009 |
| EP | 0514737 A1 | 11/1992 |
| EP | 0606634 A1 | 7/1994 |
| EP | 1213316 A2 | 6/2002 |
| EP | 1350804 A1 | 10/2003 |
| EP | 1520870 A1 | 4/2005 |
| EP | 1550687 A1 | 7/2005 |
| EP | 2243799 A1 | 10/2010 |
| WO | 2009010527 A1 | 1/2009 |
| WO | 2011/134869 A2 | 11/2011 |
| WO | 2013/103147 A1 | 7/2013 |
| WO | 2018/015152 A1 | 1/2018 |

* cited by examiner

METHOD FOR PRODUCING SILOXANES CONTAINING GLYCERIN SUBSTITUENTS

CROSS REFERENCE TO RELATED APPLICATIONS

This application is a 35 U.S.C. § 371 U.S. national phase entry of International Application PCT/EP2017/066756 having an international filing date of Jul. 5, 2017, which claims the benefit of European Application No. 16180762.3 filed Jul. 22, 2016, each of which is incorporated herein by reference in its entirety.

FIELD

The invention relates to a method for preparing siloxanes having glycerol modifications and also at the same time hydrophobic substituents. The present invention further relates to a siloxane having glycerol modifications and also hydrophobic side chains, wherein the glycerol modifications bear at least partially ketal groups, and also the use of these novel siloxanes.

Organomodified siloxanes are used in various applications. Their properties can be adjusted by the type of modification and also by the specific modification density.

The noble metal-catalysed hydrosilylation reaction represents a universal methodology for the SiC bond forming modification of siloxane skeletons having SiH groups.

For instance, in this manner, with allyl polyethers for example, organophilic or non-ionic hydrophilic groups may be bonded to a siloxane skeleton. Such compounds are used, for example, as polyurethane foam stabilizers and as defoamers in propellants.

In contrast, by reaction with α-olefins, the siloxane can be attached to lipophilic groups. The silicon waxes obtained thereby serve, for example as additives in cosmetic applications.

Since polyether-containing compounds have come under increasing criticism in recent times, there exists a need for siloxane-based emulsifiers which bear no polyether groups but at the same time have good emulsifying and dispersing properties.

For this purpose, glycerol or polyglycerol derivatives are used to replace the polyether groups as hydrophilic component. Polyglycerol-modified siloxanes of this kind are described, for example, in EP 1213316. In the application EP 1550687, glycerol-modified siloxanes are used for application in emulsions.

EP 1550687 discloses that glycerol-modified, particularly polyglycerol-modified siloxanes may be prepared directly by hexachloroplatinic acid-catalyzed SiC linkage of lateral hydrogen siloxanes with polyglycerol mono- or polyglycerol diallyl ethers in isopropanol as reaction medium. In this case, SiOC linked hydrolysable secondary products are inevitably formed.

EP2243799 addresses this problem and teaches that the weaknesses of systems known hitherto can thus be prevented by carrying out the linkage of the glycerol derivative not in comb positions but at the termini of the siloxane skeleton to be modified.

Despite the teaching presented in this document, no technical solution for the preparation of high-purity glycerol-modified siloxanes is presented. The general procedure described therein for the preparation of alkyl/glycerol-modified siloxanes follow in that stoichiometric excesses of α-olefin and glycerol monoallyl ether and 10 ppm Karstedt's catalyst are initially charged in ca. 30% toluene (based on the total weight) with stirring and heated to 95° C. The hydrogen siloxane is then added dropwise at 95° C. over 2 hours. After distillative workup of the reaction mixture having complete SiH conversion (stripping off volatile components at 110° C. and with the aid of an applied vacuum of ca. 1 mbar), a viscous, slightly cloudy, almost colorless product is obtained.

The use of aromatic solvent is of sufficient disadvantage for this method if the resulting siloxane is intended to be used as a cosmetic additive. In addition, by means of the reaction regime, in which an ambident substrate such as glycerol monoallyl ether is combined with the SiH siloxane in the presence of a platinum catalyst, hydrolytically unstable SiOC linked secondary products are formed. These secondary products, due to their chemical relationship to the main products and their non-volatility, are not separable from the product and therefore remain therein. Nonetheless, secondary product formation accounts for up to ca. 25 val % of the glycerol monoallyl ether used.

As a result, the achievable selectivity for the SiC linkage always lags behind that theoretically expected.

Recognising the difficulty resulting from the presence of the ambident substrate, the teaching of WO 2011134869 is directed to the use of 1,2-O-isopropylidene-3-allyloxy-1,2-propanediol as modifying reagent of comb-like structured SiH siloxanes (Examples 1a, 2a, 3a). Although only the ketal moiety is to be added as sole substituent on the respective hydrogen siloxane, the use of a large amount of dioxane is necessary (ca. 78% in Example 1a, ca. 71% in Example 2a and ca. 57% in Example 3a) in order to isolate after more than 24 hours yields of 88 to 92% of the glycerol-modified siloxane still to be protected.

The object given to providing diacrylate group-bearing siloxanes for use in radiation-curing systems, U.S. Pat. No. 4,908,228 addresses the reaction of 1,2-O-isopropylidene-3-allyloxy-1,2-propanediol with hydrogen silanes and hydrogen siloxanes and limits itself in this case to the consideration of purely binary substance systems. The glycerol ketal-modified silanes and siloxanes obtained are subsequently subjected to a hydrolysis or alcoholysis and the diol-modified siloxanes released are acrylated.

SUMMARY

The object of the invention was to provide a method with which glycerol-modified siloxanes can be prepared without the use of relatively large amounts of solvent, which additionally have hydrophobic substituents.

DETAILED DESCRIPTION

It has now been found, surprisingly, that the method described below for preparing siloxanes having glycerol modifications and at the same time hydrophobic substituents, may be a carried out without large amounts of solvent. Completely surprisingly, the reactants used in the method according to the invention result in an unforseeably high phase compatibility. Typically, hydrosilylation reactions carried out without solvent are characterized by a substrate-dependent incompatibility, which leads to the fact that the SiC linkage reaction starts from the multiphasic state, generally from a biphasic state. The silicone phase having SiH groups and the olefinic reaction partner to be added on have no affinity due to their different polarities from each other and are in addition separated more by density differences. For instance, the solvent-free SiC linkage reaction between SiH siloxanes and unsaturated (poly)ethers can be cited, which always begins biphasically. With the starting formation of the SiC linked copolymer, a phase-compatibilizing surfactant is present which promotes the dispersal of the reaction partners at the phase interface. With the product concentration increasing during the reaction course, the concentration of incompatible reactants falls, which permeate the reaction matrix in the form of small droplets. At the so-called clearing point, the diameter of the individual droplets of the incompatible dispersed phase has fallen below the wavelength of visible light and the previously cloudy reaction matrix appears to the naked eye to be a clear phase.

Knowing the practical experiences in the SiC bond forming (poly)ether modification of siloxanes, phase compatibility of the addenda in the hydrosilylation step in the preparation of the inventive claimed siloxanes bearing simultaneously glycerol, glycerol ketal and hydrophobic substituents represents a surprise to those skilled in the art, since formally glycerol monoallyl ether ketal—detached from its preparation and questions of nomenclature—is considered as an unsaturated (poly)ether compound having 3 ether oxygen atoms. In place of the biphasicity of the reaction matrix usually observed in (poly)ether additions—and from the start of the hydrosilylation—an undifferentiated clear homogeneous phase is apparent to the naked eye. For operational practice, this system behavior is of exceptional importance, since it avoids the necessity to use solvent and/or to attach the reaction partners to the polymer skeleton in a complex sequence, as is described, for example, in the production Example 1 of WO2013103147, page 49 ff.

The present invention therefore relates to a method for preparing modified siloxanes comprising the method steps of
A) providing a hydrogen siloxane having at least three SiH groups per molecule;
B) hydrosilylation of the hydrogen siloxane with
  at least one α-olefinic hydrocarbon having 2 to 36, particularly 8 to 28, carbon atoms and
  at least one ketalized glycerol derivative comprising:
    a glycerol skeleton and
    one α-olefinic coupling group; and optionally
C) purifying the hydrosilylated siloxane; and optionally
D) at least partial acidic hydrolysis of the ketals present in the ketalized glycerol derivatives reacted with the hydrogen siloxane.

The invention further relates to a modified siloxane obtainable by the aforementioned method, and also the use of the same as emulsifier.

An advantage of the method according to the present invention is that the glycerol-modified siloxanes with regard to SiOC linked secondary products can be prepared in high purity. A further advantage of the method according to the invention is that the glycerol-modified siloxanes obtainable are able to achieve excellent emulsions and dispersions. Such formulations are stable in storage and the emulsions or dispersions show over a period of several months and at different temperatures a constantly stable composition and homogeneity without separation of oil or water or solid. The glycerol-modified siloxanes obtainable have proven to be particularly advantageous especially in cosmetic emulsion preparations for make-up and sun protection applications, which additionally comprise inorganic pigments such as titanium dioxide or iron oxide, since the glycerol-modified siloxanes obtainable impart to these formulations a good long-term stability and a very good pigment dispersion.

A further advantage of the method according to the invention is that it affords a constant and reproducible quality of the end product, which was achievable only with difficulty, it at all, by the industrial methods for preparing glycerol-modified siloxanes known to date.

The preparation process according to the invention and the glycerol-modified siloxanes according to the invention are described below by way of example without the invention being limited to these exemplary embodiments. When ranges, general formulae or classes of compounds are specified below, these are intended to encompass not only the corresponding ranges or groups of compounds which are explicitly mentioned but also all subranges and subgroups of compounds which can be derived by leaving out individual values (ranges) or compounds. Where documents are cited for the purposes of the present description, the entire content of these is intended to be part of the disclosure of the present invention. Where, in the context of the present invention, compounds, such as siloxanes, are described which can have different units multiple times, then these can occur in random distribution (random oligomer) or arranged (block oligomer) in these compounds. Data on the number of units in such compounds are understood to be as averages, averaged over all relevant compounds, since in particular siloxanes are generally present as mixtures.

Unless stated otherwise, all percentages (%) given are percentages by mass.

The method for preparing modified siloxanes according to the invention is particularly oriented to the preparation of the siloxanes having at least one long-chain hydrocarbon group and at least one group containing glycerol.

In the context of the present invention, the term "hydrogen siloxane" or "H-siloxane" is always understood to mean SiH functional siloxane. The hydrogen siloxanes used in accordance with the invention are obtainable by methods known to those skilled in the art, for example, the equilibration such as is described in U.S. Pat. No. 7,196,153.

In the context of the present invention "ketalized" glycerol derivatives are understood to mean that OH groups of the glycerol derivative belonging to the glycerol portion have been formally converted by reaction with at least one ketone into a ketal. In this context, in the ketalized glycerol derivatives, at least some of the OH groups have been ketalized; preferably at least 5%, in particular at least 15% of the OH groups have been ketalized.

The structure of the siloxane base skeleton of the modified siloxane to be prepared by the method according to the invention is obviously determined by the hydrogen siloxane used in method step A).

The modified siloxane preferably has 20 to 300, particularly preferably 50 to 150 Si atoms per molecule.

In the siloxane skeleton, linear, branched and also dendritic siloxanes may be modified by the method according to the invention.

Appropriate dendritic siloxanes, which may be obtained by partial hydrosilylation of hydrogen siloxanes with branched siloxanes bearing olefin groups e.g. vinyltris(trimethylsiloxy)silane and may be used in method step B), are described, for example, in WO2013103147.

For instance, in analogy to the teaching of WO2013103147, a monoglycerol-modified dendritic siloxane according to the present invention can be obtained by adding vinyltris(trimethylsiloxy)silane, an α-olefin and glycerol ketal monoallyl ether, hydrosilylating for example on a lateral hydrogen siloxane and the addition product is subsequently subjected to a partial deketalization.

The addition of the olefinic reaction partner in method step B) can be sequenced in any desired sequence or preferably be carried out concertedly.

A preferred method according to the invention serves to prepare modified siloxanes of the general formula I)

$$M_{2+h+2i-a-b-c}M'_aM''_bM'''_cD_dD'_eD''_fD'''_gT_hQ_i \quad \text{general formula I)}$$

where
M=($R^1_3$ Si $O_{1/2}$),
M'=($R^1_2R^2$ Si $O_{1/2}$),
M''=($R^1_2R^3$ Si $O_{1/2}$),
M'''=($R^1_2R^4$ Si $O_{1/2}$),
D=($R^1_2$ Si $O_{2/2}$),
D'=($R^1R^2$ Si $O_{2/2}$),
D''=($R^1R^3$ Si $O_{2/2}$),
D'''=($R^1R^4$ Si $O_{2/2}$),
T=($R^1$ Si $O_{3/2}$) and
Q=(Si $O_{4/2}$),
where
$R^1$=mutually independent, identical or different, linear or branched, optionally aromatic hydrocarbon radicals having 1 to 16, preferably 1 to 7, carbon atoms, which optionally bear OH or ester functions, or tris(trimethylsiloxy)silane ethyl, preferably methyl, phenyl or tris(trimethylsiloxy)silane ethyl, in particular methyl or tris(trimethylsiloxy)silane ethyl,
$R^2$=mutually independent, identical or different, linear or branched, optionally aromatic hydrocarbon radicals having 2 to 36 carbon atoms, preferably 8 to 28 carbon atoms, preferably linear alkyl radicals having 8 to 28 carbon atoms, particularly n-dodecyl or n-hexadecyl, and
$R^3$=mutually independent, identical or different, selected from glycerol-containing radicals,
$R^4$=mutually independent, identical or different, selected from ketalized glycerol-containing radicals,
where
a=0 to 7, particularly 0 to 3,
b=0 to 7, particularly 0 to 3,
c=0 to 7, particularly 0 to 3,
d=10 to 200, preferably 20 to 150, particularly 50 to 130,
e=1 to 130, preferably 5 to 80, particularly 8 to 40,
f=0 to 75, preferably 1 to 45, particularly 1 to 25,
g=0 to 75, preferably 1 to 45, more particularly 4 to 25,
h=0 to 10, preferably 0 to 5, especially 0
i=0 to 5, preferably 0 to 2, particularly 0,
with the proviso that c+g>0.

The result of this for the method according to the invention, as already explained above, is that preferably such hydrogen siloxanes are provided in method step A) which correspond to the aforementioned general formula I), in which $R^2$, $R^3$ and $R^4$=H.

It is apparent that the α-olefinic hydrocarbon used in method step B) determines the structure of the radical $R^2$ and the ketalized glycerol derivative used in method step B) determines the structure of the radical $R^3$ and $R^4$.

In method step B) therefore, preferably linear α-alkenes having 8 to 28 carbon atoms, in particular n-dodecene or n-hexadecene are used as α-olefinic hydrocarbons.

In the context of the present invention, it is apparent that the radical $R^3$ is a glycerol-containing radical, which clearly has not been ketalized to $R^4$.

The term "glycerol-containing radical" in the context of the present invention is understood to mean a substituent which comprises the structure —OCH$_2$CH(O—)CH$_2$O—.

Analogous structures are understood in the context of the present invention under the term "glycerol skeleton".

In method step B), the hydrosilylation of the hydrogen siloxane with the α-olefinic hydrocarbon and the ketalized glycerol derivative can be carried out simultaneously or separately from one another, i.e. in any successive sequence, although it is preferred in accordance with the invention if in method step B) the hydrosilylation of the hydrogen siloxane is carried out with a mixture comprising the α-olefinic hydrocarbon and the ketalized glycerol derivative.

In method step B), the hydrosilylation can be carried out in the presence of a catalyst according to established methods. It is possible to use, for example, catalysts such as complexes of platinum, rhodium, osmium, ruthenium, palladium, iridium or similar compounds or the corresponding pure elements or derivatives thereof immobilized on silica, aluminium oxide or activated carbon or similar support materials. The hydrosilylation is preferably carried out with the aid of platinum complexes such as cis-(NH$_3$)$_2$PtCl$_2$ (cisplatin), di-μ-[chlorobis chloro(cyclohexene)platinum (II)] or [tris(divinyltetramethyldisiloxane)bisplatin(0)] (Karstedt's catalyst) and particularly preferably with olefin-activated platinum(0) complex catalysts (so-called WK catalysts) according to the teaching of EP1520870. The amount of catalyst is calculated in this case such that the total concentration of platinum is from 1 to 100 wppm, based on the total reaction mixture. As is apparent to those skilled in the art, the minimum platinum concentration is selected so that a rapid SiC bond forming reaction is ensured, without the economic viability of the method being affected by excessively high noble metal use or by also causing disadvantageous product discolorations. The hydrosilylation may be carried out at temperatures between 0 and 200° C., preferably between 50 and 140° C. The reaction may be carried out in suitable solvents such as aliphatic or aromatic hydrocarbons, cyclic oligosiloxanes, alcohols, carbonates or esters. Suitable processes for hydrosilylation are described, for example, in the book "Chemie und Technologie der Silicone" [Chemistry and Technology of the Silicones], Verlag Chemie, 1960, page 43, and in U.S. Pat. No. 3,775,452, to which express reference is made.

In contrast to the methods known to date, the use of a solvent can be omitted in method step B).

It is therefore preferred according to the invention that in method step B) at most 20% by weight, preferably at most 10% by weight, in particular at most 5% by weight solvent is used, wherein the percent by weight refers to the sum total of hydrogen siloxane, α-olefinic hydrocarbon, ketalized glycerol derivative and solvent.

The ketalized glycerol derivative preferably used in method step B) is derived structurally preferably by ketalizing with substances selected from the group R'—(CO)—R" where R' and R" are identical or different hydrocarbon radicals, in particular alkyl groups having 1 to 10 carbon atoms, benzaldehyde, cyclopentanone, cyclohexanone and cycloheptanone.

The boiling point differences of the ketalization reagents used and considering conversion products thereof, it has proven advantageous in practice if the preparation of the ketalized glycerol derivative is not carried out using the corresponding ketone itself, but with corresponding ketals thereof. Preference is given to using dimethoxy or diethoxy ketals in this case.

Methods for preparing cyclic acetals and ketals are disclosed in DE19648960 and in DE19647395. Directions for carrying out the ketalization over solid catalysts are disclosed, for example, in DE102008015756. WO2009010527 relates to a method for preparing cyclic glycerol acetals or cyclic glycerol ketals or mixtures of the same.

In method step B) preferably a ketalized glycerol derivative is used having the general formula II)

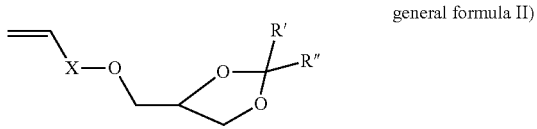

general formula II)

where R' and R" are identical or different hydrocarbon radicals, in particular alkyl groups having 1 to 20, in particular 1 to 4, carbon atoms, wherein R' and R" can be covalently bonded to each other via a C—C bond, and X is selected from divalent hydrocarbon radicals, in particular alkylene groups having 1 to 10 carbon atoms, where x=CH$_2$ is particularly preferred.

In the case that R' and R" are covalently bonded to each other via a C—C bond, the sum total of the carbon atoms of R' and R" is preferably 4 to 7 carbon atoms, especially preferably 4 carbon atoms, particularly preferably R' and R" together are in the form of an alkylene group having 4 to 7 carbon atoms.

In method step B), very particular preference is given to using a ketalized glycerol derivative of the general formula II) where x=CH$_2$ and R' and R"=CH$_3$.

Particularly preference is given to using the aforementioned preferred ketalized glycerol derivative in connection with a method according to the invention for preparing siloxanes of the general formula I) where R$^1$=methyl,
R$^2$=in particular n-dodecyl or n-hexadecyl,
and
a=0 to 3,
b=0 to 3,
c=0 to 3,
d=50 to 130,
e=8 to 40,
f=1 to 25,
g=0.5 to 25, preferably 1 to 25,
h=0, and
i=0.

It can be of advantage if the modified siloxane is purified after method step B). This is achieved preferably by distilling off of excess α-olefinic hydrocarbons and ketalized glycerol derivatives and optionally solvent.

In method step C), the ketals present in the modified siloxane are optionally at least partially acid hydrolyzed. Appropriate directions for carrying out the acidic hydrolysis are disclosed, for example, in WO2011134869.

The hydrolysis is carried out by addition of an aqueous acidic solution, in particular a toluenesulphonic acid solution. It is advantageous and therefore preferred in accordance with the invention, if method step C) is carried out at a temperature of 40° C. to 100° C.

Of all possible preferences according to the invention, method step C) is carried out such that the degree of ketalization is from 5% to 70%, preferably 10% to 40%, particularly preferably 15% to 25%, wherein the percentage refers to all diols suitable for ketalization present in the siloxane. The degree of ketalization can be determined with the aid of $^1$H-NMR spectroscopy.

By way of preference in accordance with the invention, the method according to the invention can include a further method step D) in which the modified siloxane is purified.

Method step D) according to the invention preferably includes neutralization of the acid used for the acidic hydrolysis in method step C), followed by removal of the salts thus formed. This is preferably carried out according to the invention in the form of a filtering off of the salt. Also preferred in accordance with the invention is a distillative removal of the further substances added in step C) and predicted by-products formed. These include particularly water and ketones.

The present invention further relates to siloxanes obtainable by the method according to the invention which are characterized in that they have at least one ketalized glycerol-containing radical.

Particularly preferred in accordance with the invention are modified siloxanes of the general formula I)

$$M_{2+h+2i-a-b-c}M'_aM''_bM'''_cD_dD'_eD''_fD'''_gT_hQ_i$$  general formula I)

with
M=(R$^1_3$ Si O$_{1/2}$),
M'=(R$^1_2$R$^2$ Si O$_{1/2}$),
M"=(R$^1_2$R$^3$ Si O$_{1/2}$),
M'''=(R$^1_2$R$^4$ Si O$_{1/2}$),
D=(R$^1_2$ Si O$_{2/2}$),
D'=(R$^1$R$^2$ Si O$_{2/2}$),
D"=(R$^1$R$^3$ Si O$_{2/2}$),
D'''=(R$^1$R$^4$ Si O$_{2/2}$),
T=(R$^1$ Si O$_{3/2}$) and
Q=(Si O$_{4/2}$),
where
R$^1$=mutually independent, identical or different, linear or branched, optionally aromatic hydrocarbon radicals having 1 to 16, preferably 1 to 7, carbon atoms, which optionally bear OH or ester functions, or tris(trimethylsiloxy)silane ethyl, preferably methyl, phenyl or tris(trimethylsiloxy)silane ethyl, in particular methyl or tris(trimethylsiloxy)silane ethyl,
R$^2$=mutually independent, identical or different, linear or branched, optionally aromatic hydrocarbon radicals having 2 to 36 carbon atoms, preferably 8 to 28 carbon atoms, preferably linear alkyl radicals having 8 to 28 carbon atoms, particularly n-dodecyl or n-hexadecyl, and
R$^3$=mutually independent, identical or different, selected from glycerol-containing radicals,
R$^4$=mutually independent, identical or different, selected from ketalized glycerol-containing radicals,
where
a=0 to 7, particularly 0 to 3,
b=0 to 7, particularly 0 to 3,
c=0 to 7, particularly 0 to 3,
d=10 to 200, preferably 20 to 150, particularly 50 to 130,
e=1 to 130, preferably 5 to 80, particularly 8 to 40,
f=0 to 75, preferably 1 to 45, particularly 1 to 25,
g=0 to 75, preferably 1 to 45, more particularly 4 to 25,
h=0 to 10, preferably 0 to 5, especially 0
i=0 to 5, preferably 0 to 2, particularly 0,
with the proviso that c+g>0.

Particularly preferred siloxanes according to the invention are characterized in that in the general formula I)

R$^1$=methyl,
R$^2$=in particular n-dodecyl or n-hexadecyl, and

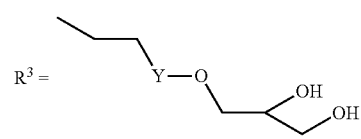

where Y=[CH$_2$]$_s$, where s=1 to 5, particularly 1,

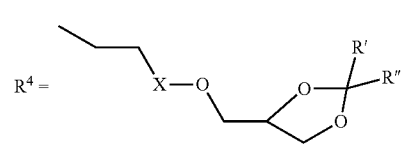

where x=[CH$_2$]$_r$, where r=1 to 5, particularly 1, and R' and R"=mutually independent, identical or different linear alkyl having 1 to 4 carbon atoms, wherein R' and R" can be covalently bonded to each other via a C—C bond, in particular CH$_3$,
and
a=0 to 3,
b=0 to 3,
c=0 to 3,
d=50 to 130,
e=8 to 40,
f=1 to 25,
g=0.5 to 25, preferably 1 to 25,
h=0, and
i=0.

The modified siloxanes according to the invention can be used advantageously as emulsifier since they have excellent surface-active properties.

Therefore, the present invention further relates to the use of the modified siloxanes according to the invention as emulsifier. Modified siloxanes of the present invention depicted above as preferred in accordance with the present invention are preferably used corresponding to their preference according to the invention.

The use according to the invention is preferably in pharmaceutical or cosmetic formulations. This is particularly therefore of advantage since the modified siloxanes according to the invention can be prepared free of irritating organic solvents and thus have a high purity at the end of the preparation.

For the use according to the invention as emulsifier it is particularly preferable that the modified siloxane of the general formula I) according to the invention meets the proviso that
N=2+d+e+f+g+2h+3i=51 to 350, preferably 60 to 250, in particular 65 to 180,
y=(a+c+e+g)/(b+f)=0.5 to 25, preferably 2 to 20, in particular 3 to 10, and
z=a+b+c+e+f+g=greater than/equal to 10, preferably greater than 12, in particular, greater than 14.

The aforementioned particularly preferred modified siloxane used in accordance with the invention is a preferred siloxane according to the invention of the present invention.

The examples adduced hereinafter describe the present invention by way of example, without any intention that the invention, the scope of application of which is apparent from the entirety of the description and the claims, be restricted to the embodiments specified in the examples.

EXAMPLES

Example 1: Ketalization of Glycerol Monoallyl Ether

In a 1 l multi-necked flask equipped with KPG stirrer, internal thermometer and reflux condenser, 300 g of glycerol monoallyl ether GAE (MW: 132.16 g/mol) together with 354.6 g of 2,2-dimethoxypropane DMP (MW: 104.15 g/mol; b.p.: 83° C.; 50% excess) are initially charged at 20° C. and then 0.33 g of p-toluenesulphonic acid p-TSA (0.05% based on GAE and DMP) added and the mixture heated at reflux temperature for one hour. The reflux condenser is then replaced by a distillation system. Over the course of 4 hours a slow reduction in distillate takes place, whereupon the distillate temperature increases up to 80° C. After cooling the bottom, 13 g of sodium hydrogen carbonate are added over the course of 30 minutes to neutralize the acid. The salt is removed by means of a pleated filter (MN 615 1/4) and the filtrate is freed from volatiles on a rotary evaporator at 60° C. and a pressure of <1mbar. The $^1$H-NMR spectrum of the colorless clear liquid demonstrates quantitative ketalization.

Example 2: Hydrosilylation of a Hydrogen Siloxane with 1-Dodecene and Glycerol Monoallyl Ether Ketal In a 1 l multi-necked flask equipped with KPG stirrer, internal thermometer and reflux condenser, 96.6 g of the 28 val % glycerol monoallyl ether ketal prepared in Example 1; MW: 172.2 g/mol; 30% excess) together with 243.9 g of dodecene (72 val %; MW: 168.9 g/mol; 30% excess) are initially charged with stirring at 20° C. and heated to 60° C. The mixture of both components forms a clear phase. 237.2 mg of a Karstedt catalyst activated with ethylene dissolved in decamethylcyclopentasiloxane according to the teaching of EP 1520870 B1 (1% Pt dissolved in Ds, ethylene sparged corresponding to 3 ppm Pt based on the total mixture) are added and then 450 g of a hydrogen siloxane, which has both pendant and terminal SiH functions and an average chain length N=120 (SiH value: 3.43 mmol SiH/g) are added dropwise over 30 minutes. The exotherm which occurs heats the reaction mixture, which remains clear, over the whole period of the addition to 90° C. The reaction is allowed to proceed for 4 hours at 90° C.

The gas volumetric SiH determination (decomposition of a weighed sample aliquot in a gas burette by addition of sodium butoxide solution and measurement of the hydrogen volume released) shows a SiH conversion of 99.1%. The crude product is freed from volatiles on a rotary evaporator at 130° C. and at an applied vacuum of <1 mbar. A clear pale yellow liquid is isolated. A $^1$H-NMR spectrum confirms the desired structure.

Example 3: Deketalization/Partial Hydrolysis of the Precursor Prepared in Example 2

In a 250 ml multi-necked flask equipped with internal thermometer and reflux condenser, 5 g of a 5% aqueous toluenesulphonic acid solution are added with stirring to 100 g of the precursor prepared in Example 2 and the mixture is heated to 80° C. with further continuous stirring for 6 hours. After cooling the reaction mixture to 20° C., 5 g of sodium hydrogen carbonate are added to neutralize the acid. This mixture is allowed to react for ca. 30 minutes before the salt is removed with the aid of a filter press (Seitz K300 filter sheet) and the filtrate is freed of volatile constituents at 80° C. and an applied vacuum of <1 mbar.

The $^1$H-NMR spectrum assigns a degree of deketalization of ca. 83% to the colorless clear product.

Analogous to the reaction sequence outlined in Examples 1 to 3, comprising the ketalization, the hydrosilylation and the deketalization, Examples 4 to 8 are carried out, where each example in the attached Table is represents the whole reaction sequence.

The abbreviation Dk indicates the degree of Deketalization adjusted for the individual structure type, i.e. the ratio of opened to unopened ketal structure in percent, as can be determined from the respective associated $^1$H-NMR spectrum.

| | Example | | | | | |
|---|---|---|---|---|---|---|
| | 3 | 4 | 5 | 6 | 7 | 8 |
| $M_{2+h+2i-a-b-c}$ | $2+h+2i-a-b-c=1$ | $2+h+2i-a-b-c=1$ | $2+h+2i-a-b-c=1$ | $2+h+2i-a-b-c=2$ | $2+h+2i-a-b-c=2$ | $2+h+2i-a-b-c=3$ |
| $M'_a$ | a = 0.725 | a = 0.725 | a = 0.725 | a = 0 | a = 0 | a = 0 |
| $M''_b$ | b = 0.228 | b = 0.058 | b = 0.052 | b = 0 | b = 0 | b = 0 |
| $M'''_c$ | c = 0.047 | c = 0.217 | c = 0.222 | c = 0 | c = 0 | c = 0 |
| $D_d$ | d = 89 | d = 89 | d = 89 | d = 34 | d = 34 | d = 89 |
| $D'_e$ | e = 21 | e = 21 | e = 21 | e = 10 | e = 10 | e = 21 |
| $D''_f$ | f = 6.64 | f = 1.68 | f = 1.52 | f = 3.2 | f = 1.68 | f = 6.96 |
| $D'''_g$ | g = 1.36 | g = 6.32 | g = 6.48 | g = 0.8 | g = 2.32 | g = 1.04 |
| $T_h$ | h = 0 | h = 0 | h = 0 | h = 0 | h = 0 | h = 1 |
| $Q_i$ | i = 0 | i = 0 | i = 0 | i = 0 | i = 0 | i = 0 |
| $R^1$ | =CH$_3$ | =CH$_3$ | =CH$_3$ | =CH$_3$(99%) = TTMSS(1%)[3] | =CH$_3$ | =CH$_3$ |
| $R^2$ | =C$_{12}$H$_{25}$ | =C$_{12}$H$_{25}$ | =C$_{12}$H$_{25}$ | =C$_{16}$H$_{33}$ | =C$_{12}$H$_{25}$ | =C$_{12}$H$_{25}$ |
| $R^3$ | X = CH$_2$ R' = CH$_3$ R" = CH$_3$ | X = CH$_2$ [R'R"] = —(CH$_2$)$_4$—[1] | X = CH$_2$ [R'R"] = —(CH$_2$)$_5$—[2] | X = CH$_2$ R' = CH$_3$ R" = CH$_3$ | X = CH$_2$ R' = C$_{15}$H$_{31}$ R" = C$_{15}$H$_{31}$ | X = CH$_2$ R' = CH$_3$ R" = CH$_3$ |
| Dk | 83% | 21% | 19% | 80% | 42% | 87% |

[1] cyclopentanone was used for ketalization in Example 4
[2] cyclohexanone was used for ketalization in Example 5
[3] TTMSS is the tris(trimethylsiloxy)silane ethyl radical, whose presence in the dendritic siloxane skeleton is stated as a percentage proportion of all $R^1$ radicals in Example 6.

The invention claimed is:

1. A method for preparing modified siloxanes comprising the method steps of
   A) providing a hydrogen siloxane having at least three SiH groups per molecule;
   B) hydrosilyling the hydrogen siloxane with
      at least one α-olefinic hydrocarbon having 2 to 36, carbon atoms and at least one ketalized glycerol derivative comprising: a glycerol skeleton and one α-olefinic coupling group; and
   C) purifying the hydrosilylated siloxane; and
   D) at least partial acidic hydrolysis of the ketals present in the ketalized glycerol derivatives reacted with the hydrogen siloxane.

2. The method according to claim 1 for preparing modified siloxanes of the general formula I)

$$M_{2+h+2i-a-b-c}M'_aM''_bM'''_cD_dD'_eD''_fD'''_gT_hQ_i \quad \text{general formula I)}$$

where
$M=(R^1_3 \text{Si O}_{1/2})$,
$M'=(R^1_2 R^2 \text{Si O}_{1/2})$,
$M''=(R^1_2 R^3 \text{Si O}_{1/2})$,
$M'''=(R^1_2 R^4 \text{Si O}_{1/2})$,
$D=(R^1_2 \text{Si O}_{2/2})$,
$D'=(R^1 R^2 \text{Si O}_{2/2})$,
$D''=(R^1 R^3 \text{Si O}_{2/2})$,
$D'''=(R^1 R^4 \text{Si O}_{2/2})$,
$T=\text{Si O}_{3/2})$ and
$Q=(\text{Si O}_{4/2})$,
where
$R^1$=mutually independent, identical or different, linear or branched, optionally aromatic hydrocarbon radicals having 1 to 16 carbon atoms, which bear OH or ester functions, or tris(trimethylsiloxy)silane ethyl, preferably methyl, phenyl or tris(trimethylsiloxy)silane ethyl,
$R^2$=mutually independent, identical or different, linear or branched, optionally aromatic hydrocarbon radicals having 2 to 36 carbon atoms and
$R^3$=mutually independent, identical or different, selected from glycerol-containing radicals,
$R^4$=mutually independent, identical or different, selected from ketalized glycerol-containing radicals, where
a=0 to 7,
b=0 to 7,
c=0 to 7,
d=10 to 200,
e=1 to 130,
f=0 to 75,
g=0 to 75,
h=0 to 10,
i=0 to 5,
with the proviso that c+g>0.

3. The method according to claim 2, wherein in method step B) the hydrosilylation of the hydrogen siloxane is carried out with a mixture comprising the α-olefinic hydrocarbon and the ketalized glycerol derivative.

4. The method according to claim 2 for preparing modified siloxanes of the general formula I)

$$M_{2+h+2i-a-b-c}M'_aM''_bM'''_cD_dD'_eD''_fD'''_gT_hQ_i \quad \text{general formula I)}$$

wherein
$R^1$=methyl or tris(trimethylsiloxy)silane ethyl,
$R^2$=n-dodecyl or n-hexadecyl, and
and wherein
a=0 to 3,
b=0 to 3,
c=0 to 3,
d=50 to 130,
e=8 to 40,
f=1 to 25,
g=4 to 25,
h=0,
i=0.

5. The method according to claim 1, wherein in method step B) at most 20% by weight, wherein the percent by weight refers to the sum total of hydrogen siloxane, α-olefinic hydrocarbon, ketalized glycerol derivative and solvent.

6. The method according to claim 1, wherein the ketalized glycerol derivative used in method step B) is derived structurally by ketalizing with substances selected from the group R'—(CO)—R" where R' and R" are identical or different hydrocarbon radicals selected from the groups consisting of alkyl groups having 1 to 10 carbon atoms, benzaldehyde, cyclopentanone, cyclohexanone and cycloheptanone.

7. The method according to claim 1, wherein a ketalized glycerol derivative is used in method step B) having the general formula II):

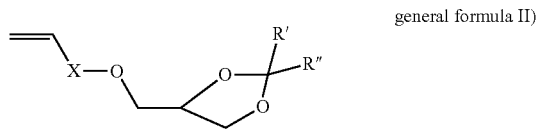

general formula II)

where R' and R" are identical or different hydrocarbon radicals, in particular alkyl groups having 1 to 10 carbon atoms, wherein R' and R" can be covalently bonded to each other via a C—C bond, and X is selected from divalent hydrocarbon radicals, in particular alkylene groups having 1 to 10 carbon atoms.

8. The method according to claim 7, wherein in method step B) a ketalized glycerol derivative of the general formula II) is used where $X=CH_2$ and R' and $R''=CH_3$.

9. The method according to claim 8 for preparing siloxanes of the general formula I) wherein $R^1$=methyl,
$R^2$=n-dodecyl or n-hexadecyl,
and
a=0 to 3,
b=0 to 3,
c=0 to 3,
d=50 to 130,
e=8 to 40,
f=1 to 25,
g=0.5 to 25,
h=0, and
i=0.

10. The method according to claim 1, wherein method step C) is carried out such that the degree of ketalization is from 5% to 70%, wherein the percentage refers to all diols suitable for ketalization present in the siloxane.

11. The method according to claim 1, further comprising method step D) of purifying the modified siloxane.

12. The method according to claim 1 wherein
B) hydrosilylation of the hydrogen siloxane with
at least one α-olefinic hydrocarbon having 8 to 28 carbon atoms.

13. The method according to claim 1, wherein method step C) is carried out such that the degree of ketalization is from 15% to 25% wherein the percentage refers to all diols suitable for ketalization present in the siloxane.

* * * * *